United States Patent
Fox (10) Patent No.: US 9,463,032 B2
(45) Date of Patent: Oct. 11, 2016

(54) METHOD AND APPARATUS FOR PERFORMING KNEE ARTHROPLASTY

(71) Applicant: Biomet Manufacturing, LLC, Warsaw, IN (US)

(72) Inventor: Duke A. Fox, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 413 days.

(21) Appl. No.: 14/185,056

(22) Filed: Feb. 20, 2014

(65) Prior Publication Data

US 2014/0171954 A1 Jun. 19, 2014

Related U.S. Application Data

(63) Continuation of application No. 13/025,807, filed on Feb. 11, 2011, now Pat. No. 8,672,946.

(51) Int. Cl.
*A61B 17/58* (2006.01)
*A61B 17/17* (2006.01)
*A61B 17/15* (2006.01)
*A61B 17/72* (2006.01)

(52) U.S. Cl.
CPC ............. *A61B 17/17* (2013.01); *A61B 17/157* (2013.01); *A61B 17/1764* (2013.01); *A61B 17/72* (2013.01)

(58) Field of Classification Search
CPC A61B 17/17; A61B 17/157; A61B 17/1764; A61B 17/72
USPC ............. 606/86 R–90, 96–98, 105; 600/214, 600/218–222, 235; 433/75–76
See application file for complete search history.

(56) References Cited

U.S. PATENT DOCUMENTS

| | | | |
|---|---|---|---|
| 4,567,886 A | 2/1986 | Petersen | |
| 5,002,547 A * | 3/1991 | Poggie | A61B 17/1677 606/88 |

(Continued)

FOREIGN PATENT DOCUMENTS

| | | |
|---|---|---|
| EP | 2417915 A1 | 2/2012 |
| GB | 2475491 A | 5/2011 |
| WO | WO-2007036699 A1 | 4/2007 |

OTHER PUBLICATIONS

Search Report for Application No. GB1202283.6 dated May 11, 2012.

(Continued)

*Primary Examiner* — Anu Ramana
*Assistant Examiner* — Jessica Weiss
(74) *Attorney, Agent, or Firm* — Schwegman Lundberg & Woessner, P.A.

(57) ABSTRACT

A method for preparing a femur and a tibia for receipt of a partial knee prosthesis. The method includes the following: positioning a femoral engagement member of a femoral drill guide proximate to the femur; positioning a tibial engagement member of the femoral drill guide proximate to the tibia; moving an adjuster associated with the femoral drill guide to translate at least one of the femoral engagement member or the tibial engagement member against the femur or tibia respectively to widen a joint space defined between the femur and the tibia; drilling holes in the femur using the femoral drill guide as a reference; coupling a tibial cut guide to the femoral drill guide; making a first cut in the tibia by referencing the femoral drill guide; and making a second cut in the tibia by referencing the tibial cut guide.

20 Claims, 11 Drawing Sheets

(56) References Cited

U.S. PATENT DOCUMENTS

| | | | |
|---|---|---|---|
| 5,122,144 A | 6/1992 | Bert et al. | |
| 5,234,433 A * | 8/1993 | Bert | A61B 17/154 606/102 |
| 5,520,695 A | 5/1996 | Luckman | |
| 5,540,696 A * | 7/1996 | Booth, Jr. | A61B 17/025 606/102 |
| 5,669,914 A | 9/1997 | Eckhoff | |
| 5,735,904 A * | 4/1998 | Pappas | A61B 17/154 606/102 |
| 5,860,980 A * | 1/1999 | Axelson, Jr. | A61B 17/155 606/88 |
| 5,911,723 A * | 6/1999 | Ashby | A61B 17/154 606/88 |
| 6,056,756 A | 5/2000 | Eng et al. | |
| 6,059,831 A | 5/2000 | Braslow et al. | |
| 6,494,914 B2 | 12/2002 | Brown et al. | |
| 6,969,393 B2 | 11/2005 | Pinczewski et al. | |
| 7,201,755 B2 | 4/2007 | Faoro et al. | |
| 7,335,206 B2 | 2/2008 | Steffensmeier et al. | |
| 7,527,630 B2 * | 5/2009 | Faoro | A61B 17/155 606/90 |
| 7,608,079 B1 | 10/2009 | Blackwell et al. | |
| 7,641,661 B2 | 1/2010 | Steffensmeier et al. | |
| 2003/0130665 A1 | 7/2003 | Pinczewski et al. | |
| 2006/0142774 A1 * | 6/2006 | Metzger | A61B 17/155 606/79 |
| 2006/0167460 A1 | 7/2006 | Pinczewski et al. | |
| 2006/0189998 A1 | 8/2006 | Rasmussen | |
| 2007/0162036 A1 | 7/2007 | Schifrine et al. | |
| 2007/0239167 A1 | 10/2007 | Pinczewski et al. | |
| 2009/0043309 A1 | 2/2009 | Rasmussen | |
| 2009/0043310 A1 | 2/2009 | Rasmussen | |
| 2009/0264890 A1 | 10/2009 | Duggineni et al. | |
| 2011/0046685 A1 | 2/2011 | Faure et al. | |

OTHER PUBLICATIONS

"The Oxford® Partial Knee—Surgical Technique" Biomet Orthopedics, 2009.

* cited by examiner

METHOD AND APPARATUS FOR PERFORMING KNEE ARTHROPLASTY

CROSS-REFERENCE TO RELATED APPLICATIONS

This application is a continuation of U.S. patent application Ser. No. 13/025,807 filed on Feb. 11, 2011, the entire disclosure of which is incorporated herein by reference.

FIELD

The present disclosure relates to a method and apparatus for preparing bone to receive an implant. In particular, the present disclosure relates to a method and apparatus for preparing a knee joint to receive a unicondylar knee system.

BACKGROUND

This section provides background information related to the present disclosure which is not necessarily prior art.

For various reasons, the human knee can fail or be damaged or worn at the tibial and femoral juncture. When only a medial or lateral side of the knee is affected, the damaged portions of the tibia and/or femur can be removed and each can be replaced with implants, conventionally referred to as a unicompartmental knee replacement. With respect to the tibia, the superior articulating surface of the tibia can be conventionally prepared to receive the implant by resecting a portion of the superior articulating bone surface. With respect to the femur, the inferior articulating surface can be conventionally prepared by resecting a portion of the inferior articulating surface. During these resections, it may be desirable to preserve as much of the natural femur as possible. Thus, there is a need for an apparatus and/or method for resecting the superior articulating surface of the tibia and the inferior articulating surface of the femur to preserve as much of the desired natural bone surfaces as possible.

SUMMARY

This section provides a general summary of the disclosure, and is not a comprehensive disclosure of its full scope or all of its features.

The present teachings provide for a method for preparing a femur and a tibia for receipt of a partial knee prosthesis. The method includes the following: positioning a femoral engagement member of a femoral drill guide proximate to the femur; positioning a tibial engagement member of the femoral drill guide proximate to the tibia; moving an adjuster associated with the femoral drill guide to translate at least one of the femoral engagement member or the tibial engagement member against the femur or tibia respectively to widen a joint space defined between the femur and the tibia; drilling holes in the femur using the femoral drill guide as a reference; coupling a tibial cut guide to the femoral drill guide; making a first cut in the tibia by referencing the femoral drill guide; and making a second cut in the tibia by referencing the tibial cut guide.

The present teachings further provide for a method for preparing a femur and a tibia for receipt of a partial knee prosthesis including the following: coupling a femoral drill guide to an intramedullary rod inserted within the femur; positioning a femoral engagement member of a femoral drill guide proximate to the femur; positioning a tibial engagement member of the femoral drill guide proximate to the tibia; moving at least one of the femoral engagement member or the tibial engagement member against the femur or tibia respectively to widen a joint space defined between the femur and the tibia; coupling a tibial cut guide to the femoral drill guide; performing a first cut on the tibia while referencing a terminal cutting surface on the femoral drill guide; and performing a second cut on the tibia while referencing the tibial cut guide.

The present teachings also provide for a method for preparing a femur and tibia for receipt of a partial knee prosthesis including the following: locating a femoral drill guide adjacent a femur wherein a femoral engagement member associated with the femoral drill guide is positioned proximate the femur and a tibial engagement member associated with the femoral drill guide is positioned proximate the tibia; moving an adjuster disposed on the femoral drill guide causing at least one of the femoral and tibial engagement members to translate against the respective femur and tibia causing a joint space between the femur and tibia to widen; determining a desired joint space between the femur and tibia based on the translation; drilling lug holes in the femur using bores in the femoral drill guide as a reference; coupling a tibial cut guide having an upper cutting surface to the femoral drill guide; performing at least one cut on the tibia while referencing a terminal cutting surface on the femoral drill guide; and performing at least one cut on the tibia while referencing the tibial cut guide.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The following description of the embodiments concerning a unicondylar femoral prosthesis and related instruments are merely exemplary in nature and are not intended to limit the disclosure or its application or uses. Moreover, while the present disclosure is described in detail below with respect to a right medial unicondylar prosthesis, it will be appreciated by those skilled in the art that the present disclosure may be applied to various other types of knee joint prostheses, such as a total knee joint prosthesis.

Figure 1:
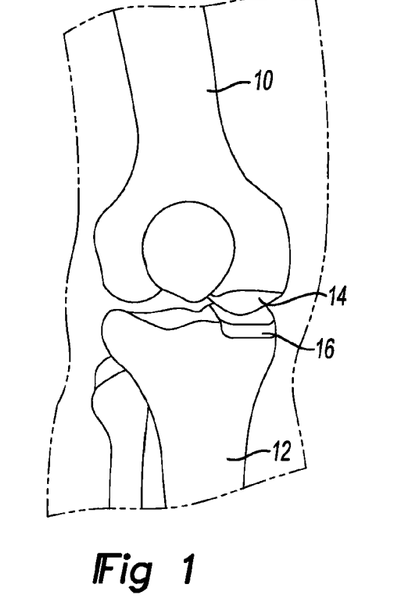
FIG. 1 is an anterior view of an exemplary unicondylar knee prosthesis implanted on a right knee according to one example of the present teachings.
Figure 2:
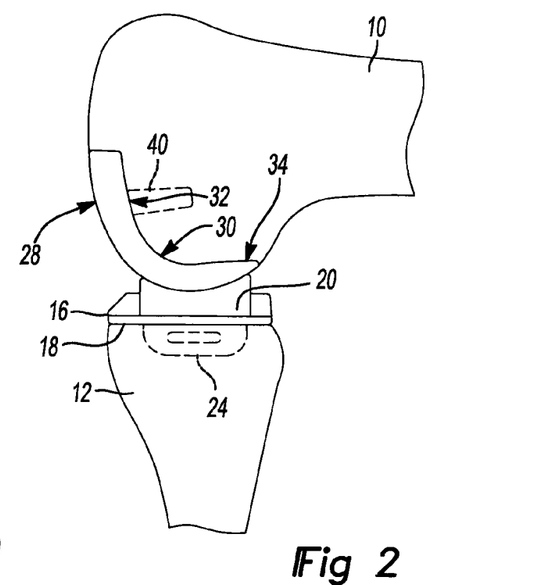
FIG. 2 is a medial view of the unicondylar femoral prosthesis of FIG. 1.

With initial reference to FIGS. 1 and 2, a unicondylar knee prosthesis implanted using the instruments and a related method of the present disclosure is shown. A femur 10 is illustrated in combination with a tibia 12. The femur 10 can have a femoral component 14 implanted therein. The tibial 12 can have a tibial component 16 implanted therein. While medial implants are shown on a right knee, it should be known that the instruments and related method will apply to both medial and lateral components, as well as left and right knees.

The tibial component 16 can include a tibial tray or platform 18 and a tibial insert or bearing 20. While the exemplary tibial component 16 is shown and described as a two-piece tibial component, the tibial component can have multiple pieces or alternatively can consist of a single unitary piece. The tibial component 16 can be designed to resurface a proximal end of the tibia 12 to cooperate with the unicondylar femoral component 14. The tibial tray 18 can include a generally D-shaped body having an attachment keel 24 extending generally orthogonally therefrom. The D-shape extends along the transverse plane. The tibial insert 20 can be constructed from any suitable bearing material, such as ultra high molecular weight polyethylene (UHMWPE). One exemplary tibial component is provided as part of the Oxford® Partial Knee marketed by Biomet Manufacturing Corp. of Warsaw, Ind.

The femoral component 14 can be designed to resurface the distal and posterior portions of one of the femoral condyles of the femur 10. The femoral component 14 can have an articulating surface 28 and a bone mating surface 30. The bone mating surface 30 can include a distal surface 32, that transitions to a posterior surface 34. Extending from the bone mating surface 30 can be a peg 40. The peg 40 can aid in alignment, stability and attachment of the femoral component 14. It can be appreciated by those skilled in the art that while the femoral component 14 has been described as having a single peg 40, other configurations are contemplated. For example, in another configuration, a femoral component can be constructed that includes two or more pegs. One exemplary femoral component is also provided as part of the Oxford® Partial Knee, identified above.

Figure 3:
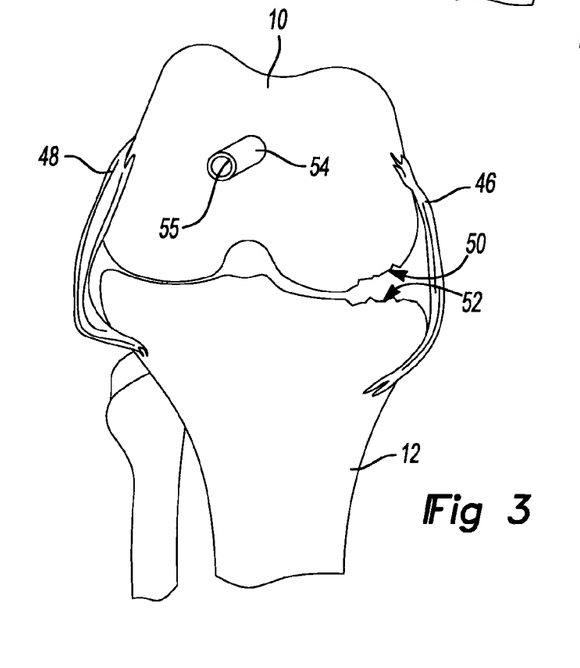
FIG. 3 is an anterior view of an exemplary knee joint shown in flexion prior to receiving the unicondylar knee prosthesis of FIG. 1.

With brief reference now to FIG. 3, a femur 10 and tibia 12 are illustrated having respective medial and lateral ligaments 46 and 48. The femur 10 can have a medial defect 50 and the tibia 12 can have a medial defect 52. As can be appreciated, such a condition can be typical for a surgeon to determine that a unicondylar knee prosthesis is suitable for implantation. According to the present teachings, an intramedullary (IM) rod 54 having a cannulation 55 can be referenced from the femur 10. The IM rod 54 can be inserted into the IM canal according to conventional methods.

Figure 4:
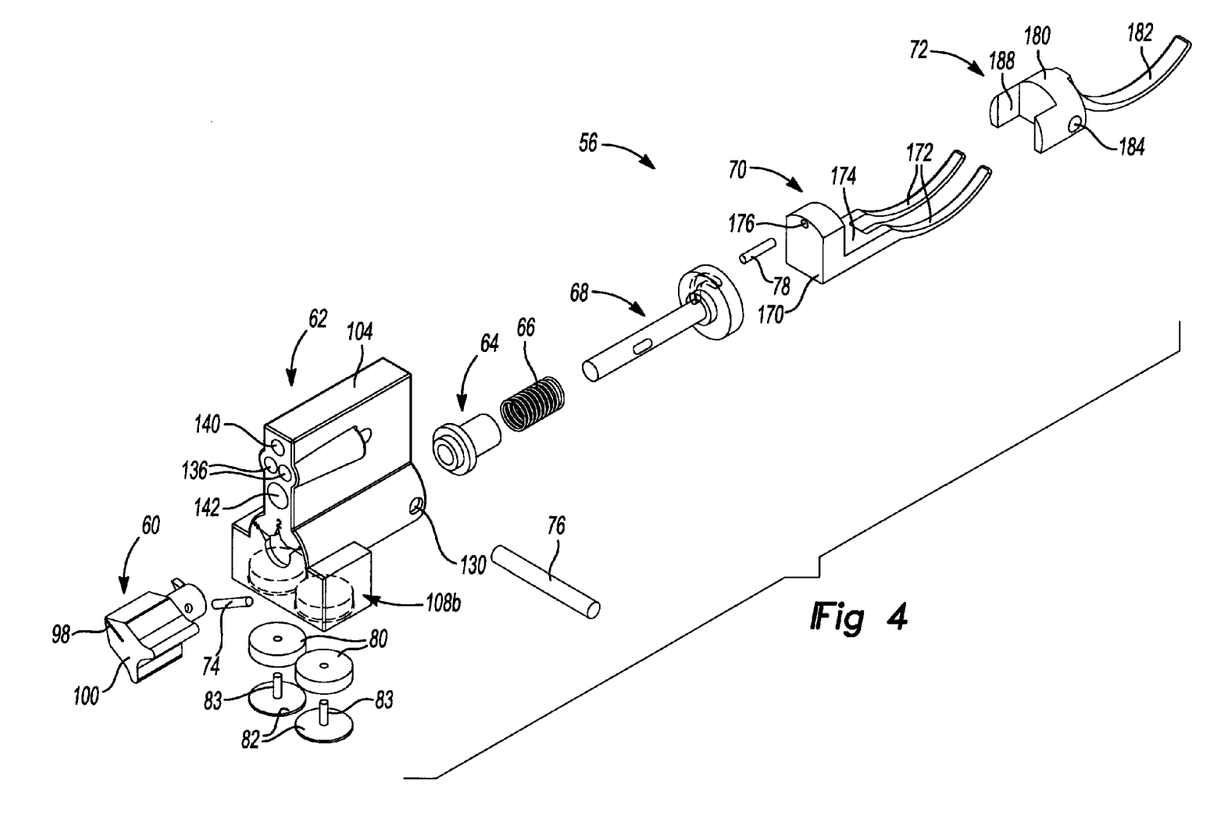
FIG. 4 is an exploded perspective view of an adjustable femoral drill guide for preparing the femur and tibia for receipt of the unicondylar knee prosthesis of FIG. 1.

Turning now to FIG. 4, an adjustable femoral drill guide 56 used for preparing the femur 10 and tibia 12 for receipt of the unicondylar prosthesis are shown. The adjustable femoral drill guide 56 can generally comprise a dial or adjuster 60, a femoral drill guide body 62, a spring capture 64, a spring or biasing member 66, a cam 68, a tibial engagement member or spoon 70 and a femoral engagement member or spoon 72. The tibial and femoral spoons 70 and 72 can both have an arcuate profile. A locating pin 74 can cooperate with the dial 60 and the cam 68. A dowel pin 76 can cooperate with the femoral drill guide body 62 and the femoral spoon 72. A cam follower 78 can cooperate with the cam 68 and tibia spoon 70 as will be described in greater detail herein. A pair of magnets 80 can be fixedly secured to the femoral drill guide body 62 by way of attachment disks 82. The attachment disks 82 can have threaded shafts that threadably mate with corresponding bores (not specifically shown) in the femoral drill guide body 62.

With continued reference to FIG. 4 and further reference now to FIG. 5, the dial 60 will be described in greater detail. The dial 60 can be used to translate the tibial spoon 70 relative to the femoral spoon 72 as will be described herein. The dial 60 can generally comprise a dial body 84 having a pointer portion 86 and a pair of lobes 88. A locating boss 90 can extend from the body 84. The locating boss 90 can generally include a cylindrical body 91 that defines an opening 92. The cylindrical body 91 can include a locating finger 94 and a transverse bore 96 that extend through diametrically opposing walls of the locating boss 90. The bore 96 can be configured to fixedly receive the locating pin 74 therein. The locating pin 74 engages structure on the cam 68 as will be described. A mark or indicia 98 can be provided on an outer face 100 of the body 84 (FIG. 4).

Figures 5, 6:
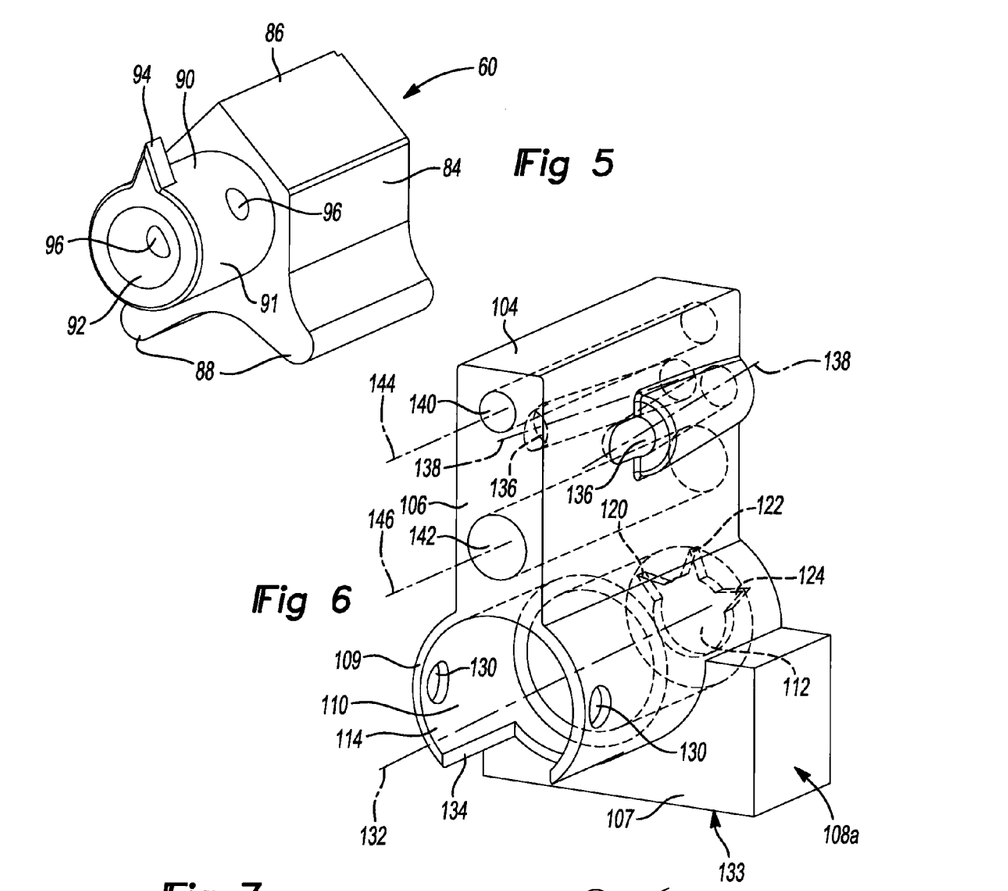
FIG. 5 is a rear perspective view of a dial of the adjustable femoral drill guide illustrated in FIG. 4.
FIG. 6 is a front perspective view of the femoral drill guide body of the adjustable femoral drill guide of FIG. 4.
Figure 19:
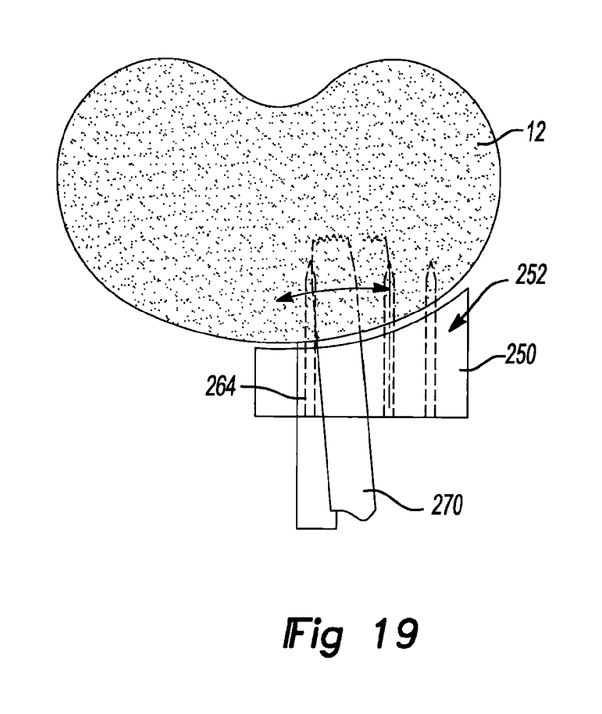
FIG. 19 is a superior view of the tibia shown with another cutting instrument performing a medial/lateral cut on the tibia.

With reference now to FIGS. 4 and 6, the femoral drill guide body 62 will be further described. The femoral drill guide body 62 can generally comprise a body 104 having a tower 106 that generally extends transversely relative to a base 107. As will become appreciated from the following discussion, the base 107 can have a terminal medial cutting surface 108a that can be configured to guide a cutting instrument such as a sagittal saw 254 for preparation of a vertical (i.e., superior/inferior) cut 260 (FIG. 19) in the tibia 12. The base 107 can also have a terminal medial cutting surface 108b (FIG. 4) that can be referenced when performing surgery on a left knee. The femoral drill guide body 62 can have a cylinder 109 that defines a bore 110. The bore 110 can be positioned generally at a transition between the tower 106 and the base 107. The bore 110 can generally define a throughbore that extends from a front or first opening 112 to a rear or second opening 114. The body 104 can include a first keyway 120, second keyway 122 and third keyway 124 at the front opening 112. The respective first, second and third keyways 120, 122 and 124 can include a shape that is generally complementary to the locating finger 94 of the dial 60. A pair of aligned side bores 130 can be formed at diametrically opposed locations in the body 104 generally transverse to a long axis 132 of the bore 110. The femoral drill guide body 62 can have a lower surface 133 that is magnetic from the magnets 80.

The cylinder 109 of the femoral drill guide body 62 can provide a cutout 134 thereon. The tower 106 can define a pair of connector holes 136 therein. The connector holes 136 define axes 138 that angle toward the nearest sidewall of the tower 106. The respective axes 138 can each angle toward the nearest sidewall an angle of about 7°. In this regard, the axes 138 can be about 14° relative to each other. As will be described, an IM rod link assembly 200 can engage one of the connector holes 136 and the cannulation 55 in the IM rod 54. The axes 138 can extend on an angle to match the angle of a typical IM canal, i.e., 7 degrees. Other angles are contemplated. Two holes 136 are provided so that the femoral drill guide body can be used for both right and left knees. A first longitudinal throughbore 140 and a second longitudinal throughbore 142 can be defined through the tower 106 of the body 104. The throughbores 140 and 142 can be formed along respective parallel longitudinal axes 144 and 146. According to one example, the axes 144 and 146 can be parallel relative to each other and parallel relative to the axis 132 of the bore 110. As will become appreciated from the following discussion, the throughbores 140 and 142 can be used to guide a cutting instrument such as a drill bit for formation of femoral peg holes 148, 149 (FIG. 14) in the femur 10 for receipt of the pegs 40 and 42, respectively (FIG. 2).

Figure 7:
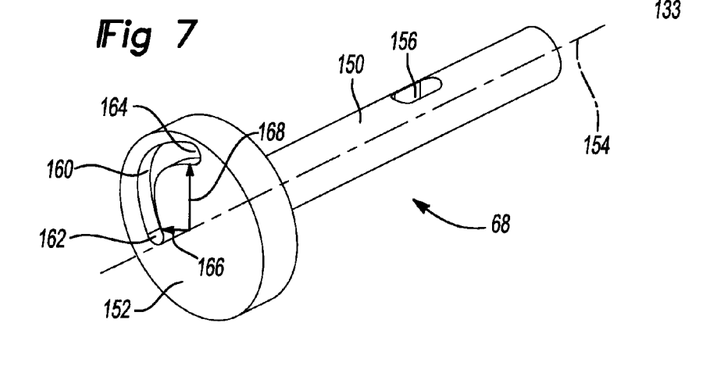
FIG. 7 is a rear perspective view of a cam of the adjustable femoral drill guide of FIG. 4.

Turning now to FIG. 7, the cam 68 will be described in greater detail. The cam 68 can generally comprise an elongated cylindrical rod 150 that extends from a center point of a disk 152. As will be described, the cam 68 can convert rotational motion of the dial 60 into linear translation of the tibial spoon 70. The rod 150 can generally be formed along a longitudinal axis 154. A slot 156 can be formed through the rod 150 for receipt of the locating pin 74 (FIG. 4). The disk 152 can include a groove 160 formed thereon. The groove 160 can generally extend in a manner having an increasing radius from a first end 162 to a second end 164. In general, the first end 162 can initiate on the disk 152 at a first distance 166 from the longitudinal axis 154. The second end 164 can terminate at a second distance 168 from the longitudinal axis 154. In this regard, the second distance 168 can be greater than the first distance 166. As will become appreciated from the following discussion, the cam follower 78 can be configured to ride along the groove 160 between the first end 162 and the second end 164 during rotation of the cam 68 around the longitudinal axis 154. Movement of the cam follower 78 along the groove 160 can cause the cam follower 78 to translate away from or toward the longitudinal axis 154, which can cause the tibial spoon 70 to translate away from or toward the femoral spoon 72.

Figures 8, 9:
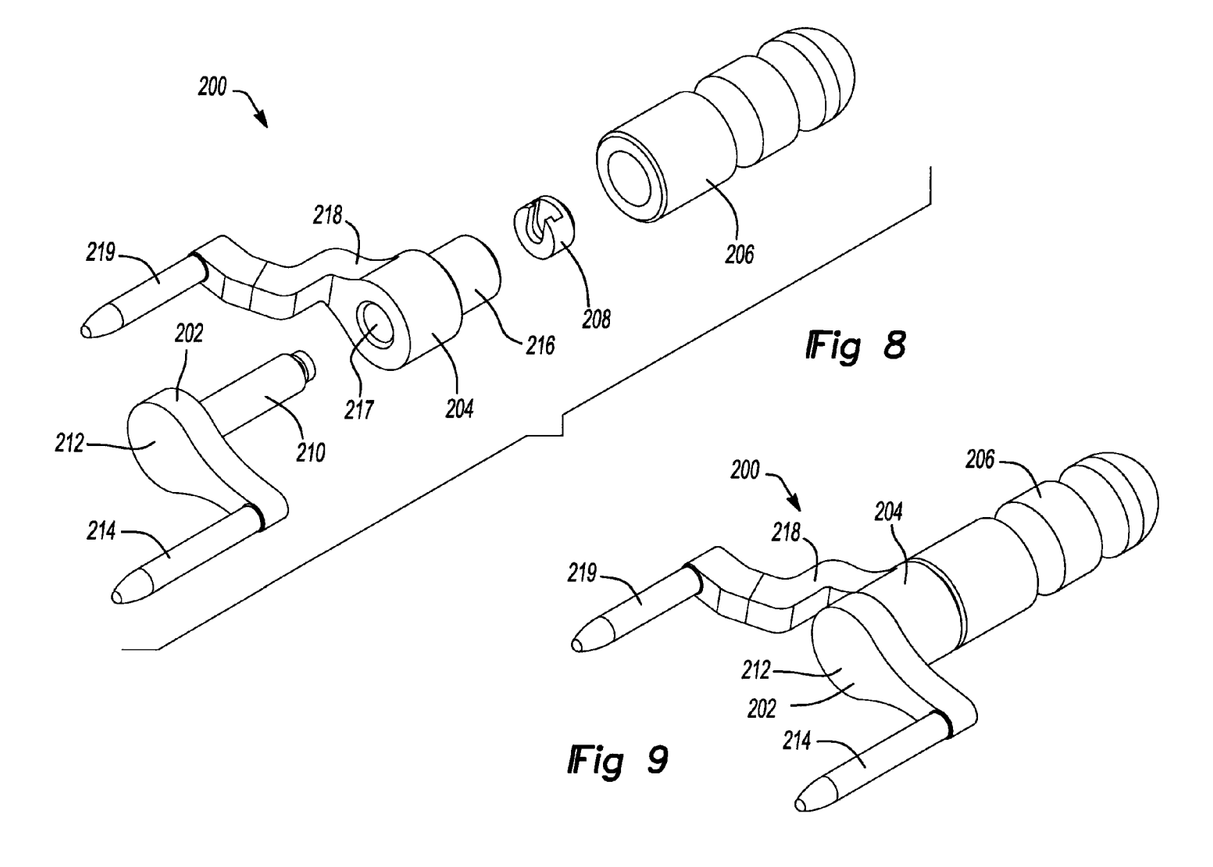
FIG. 8 is an exploded perspective view of an IM rod link assembly according to the present teachings.
FIG. 9 is a perspective view of the IM rod link of FIG. 8 shown in an assembled position.
Figure 10:
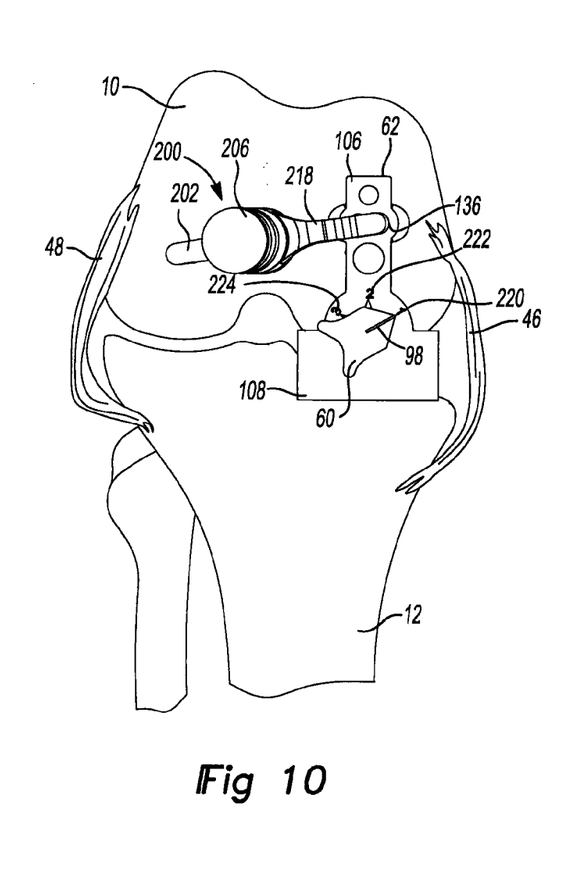
FIG. 10 is an anterior view of the knee illustrated in FIG. 3 and shown with the adjustable femoral drill guide positioned relative to the knee joint and relative to an intramedullary (IM) rod extending from the femur via an IM rod link.

Returning now with specific reference to FIG. 4, the tibial spoon 70 and femoral spoon 72 will be described in further detail. The tibial spoon 70 can generally include a heel 170 and a pair of feet 172. The feet 172 can be generally connected to the heel 170 by way of an intermediate body portion 174. An aperture 176 can be formed in the heel 170 for receipt of a portion of the cam follower 78. According to one example, the feet 172 can be curved in a profile that generally matches the posterior femur (FIG. 9). The femoral spoon 72 can generally comprise a cylindrical body portion 180 having a foot 182 extending therefrom that can engage the distal femur 10. In one advantage with the instant configuration, the foot 182 can have the same curved profile as the feet 172. Because the foot 182 is configured to locate intermediate the feet 172 prior to adjusting the dial 60 (FIG. 9), the foot 182 and feet 172 can occupy a common space in the transverse plane. In this regard, the feet 172 and foot 182 can be located into the joint space with minimal disturbance of the host bone and/or tissue. A throughbore 184 can be formed through the cylindrical body portion 180 for receipt of the dowel pin 76. More specifically, the dowel pin 76 can fixedly locate through the side bores 130 on the femoral drill guide body 62 and through the throughbore 184 to fixedly secure the cylindrical body portion 180 of the femoral spoon 72 into the bore 110. The cylindrical body portion 180 can further include a channel 188 in which the heel 170 can slidably nest. The cutout 134 (FIG. 6) on the cylinder 109 can provide a geometry that accommodates passage of the heel 170 of the tibial spoon 70.

With additional reference now to FIGS. 8-12, the adjustable femoral drill guide 56 will be described in an assembled position and relative to the femur 10 and tibia 12. According to one example, an IM rod link assembly 200 can fixedly connect the IM rod 54 to the femoral drill guide body 62. The IM rod link assembly 200 can generally comprise a first locating portion 202, a second locating portion 204, a handle portion 206 and a locking ring 208. The first locating portion 202 has a shaft 210, a connecting plate 212 and a locating peg 214. The second locating portion 204 has a body 216 having a cannulation 217, a connection plate 218 and a locating peg 219. The shaft 210 can be rotatably received by the cannulation 217. The locking ring 208 can axially fix the second locating portion 204 to the first locating portion 202. The exploded view of FIG. 8 is provided for illustrative purposes. The IM rod link assembly is provided to the user as an assembled tool that will not be disassembled by the user. In this regard, the handle portion 206 can be securely fixed, such as by welding, to the second locating portion 204 at the body 216. As will become appreciated herein, the locating peg 214 can selectively locate into the cannulation 55 and the locating peg 219 can selectively locate into one of the connector holes 136 to position the femoral drill guide relative to the IM rod 54.

Figure 11:
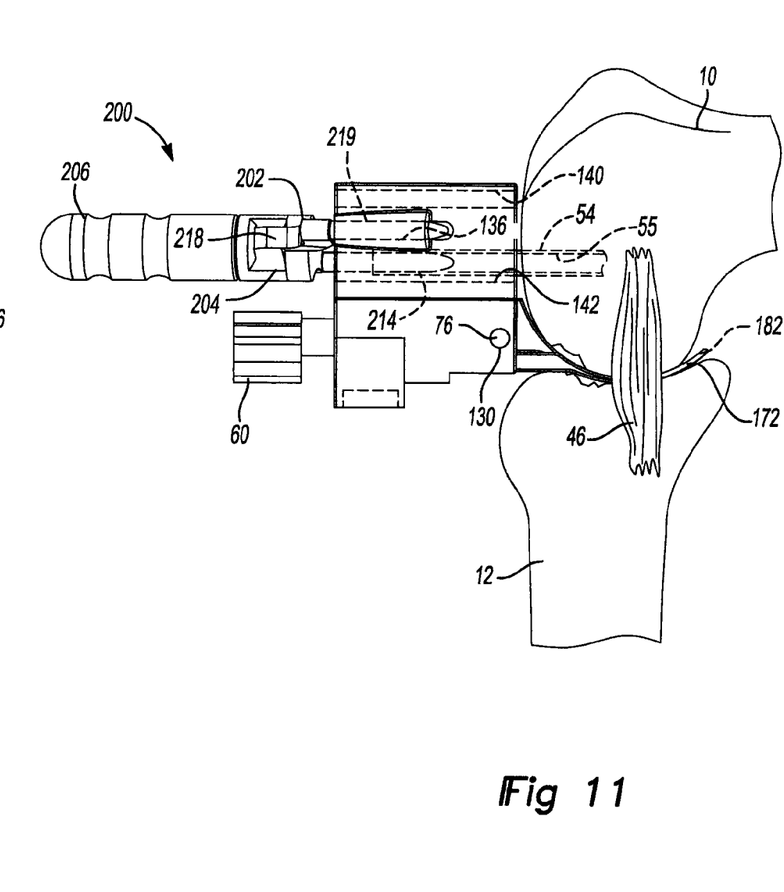
FIG. 11 is a medial view of the adjustable femoral drill guide of FIG. 10 and shown with a tibial spoon and femoral spoon extending into the joint space between the femur and tibia.

In the exemplary initial position illustrated in FIG. 11, the foot 172 of the tibial spoon 70 and the foot 182 of the femoral spoon 72 are generally aligned at the same elevation. In this regard, the foot 182 of the femoral spoon 72 can be positioned between the feet 172 of the tibial spoon 70. Again, the femoral spoon 72 is fixed relative to the femoral drill guide body 62 by way of the dowel pin 76. The tibial spoon 70 can be selectively translated downwardly as viewed in FIG. 11 or more particularly in a direction inferiorly toward the tibia 12 for increasing a gap or joint space between the femur 10 and the tibia 12. In general, rotation of the dial 60 can cause the cam follower 78 to ride around the groove 160 in the disk 152 of the cam 68 causing the cam follower 78 (connected to the aperture 176 in the heel 170 of the tibial spoon 70) to urge the tibial spoon 70 into the tibia 12 to increase the joint space between the femur 10 and tibia 12.

An exemplary method of increasing the joint space by using the adjustable femoral drill guide 56 according to one example of the present teachings will now be described with reference to FIGS. 10-13. The femoral drill guide body 62 can have a first indicia 220, a second indicia 222 and a third indicia 224 formed thereon for alignment with the mark 98 on the dial 60. According to the exemplary configuration, the corresponding indicia 220, 222 and 224 can represent one millimeter difference in spacing between the feet 172 of the tibial spoon 70 and the foot 182 of the femoral spoon 72 (e.g., one millimeter difference in joint space between the femur 10 and tibia 12).

At the outset, a user can depress the dial 60 in a direction along the longitudinal axis 154 toward the femoral drill guide body 62 against the bias of the spring 66. In this regard, the locating finger 94 can be advanced through the first keyway 120 while the locating pin 74 can travel along the slot 156 of the cam 68. This movement disengages the locating finger 94 from the keyway 120 to allow it to rotate freely. Next, the user can rotate the dial 60 in a direction counter-clockwise as viewed from FIG. 8 causing the cam 68 to rotate around the longitudinal axis 154 (FIG. 7). Rotation of the cam 68 around the longitudinal axis 154 can cause the cam follower 78 to ride around the groove 160 from a location generally at the first end 162 to a direction toward the second end 164 (or in a position generally radially inwardly). As a result, the cam follower 78 can be caused to urge the tibial spoon 70 downwardly (inferiorly into the tibia 12) as viewed in FIG. 13. Concurrently, the heel 170 can slidably translate through the channel 188 of the femoral spoon 72 and through the cutout 134 of the femoral drill guide body 62. The user can then release the dial 60 to allow the spring 66 to bias the dial 60 outwardly to locate the locating finger 94 into one of the other keyways 122 or 124.

Figure 12:
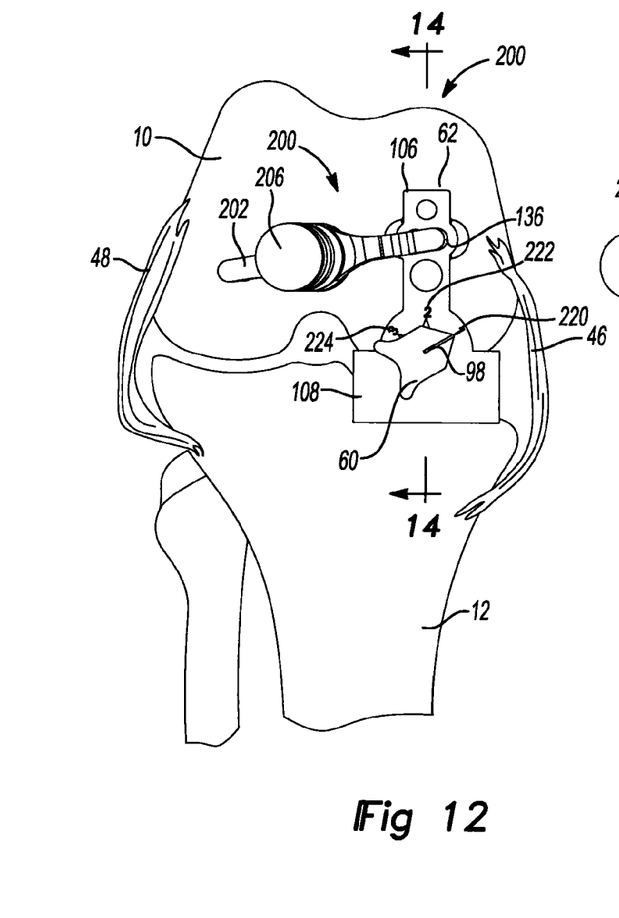
FIG. 12 is an anterior view of the knee shown in FIG. 10 and illustrated with the dial rotated to a discrete position that corresponds with the tibial spoon being translated against the tibia to widen the joint space between the femur and tibia.
Figure 13:
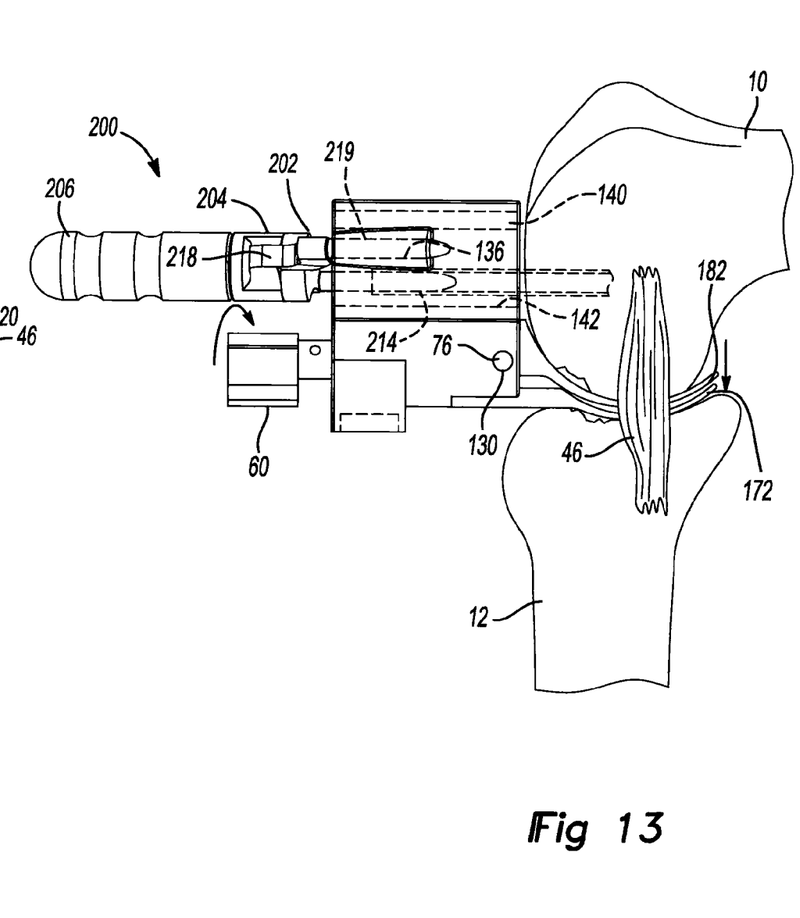
FIG. 13 is an anterior view of the adjustable femoral drill guide of FIG. 12 shown with the tibial spoon translated inferiorly against the tibia and relative to the femoral spoon that is engaged to the femur.

As illustrated in FIG. 12, the dial 60 has been released, such that the spring 66 urges the locating finger 94 into the third keyway 124 corresponding to the third indicia 224. In this position, the cam follower 78 can ride around the groove 160 to a position at the second end 164 (FIG. 7) causing the tibial spoon 70 to translate further downwardly (as viewed in FIG. 13) into the tibia causing the joint space to widen. At this time, the surgeon can determine a proper joint tension with the knee in flexion and with the respective tibial and femoral spoons 70 and 72 located against the tibia and femur as illustrated in FIG. 13. The desired offset between the respective tibial and femoral spoons 70 and 72 is now determined. While the exemplary configuration comprises an apparatus and method for moving the tibia 12 relative to the femur 10, the femur 10 can be moved additionally or alternatively relative to the tibia 12.

Figure 14:
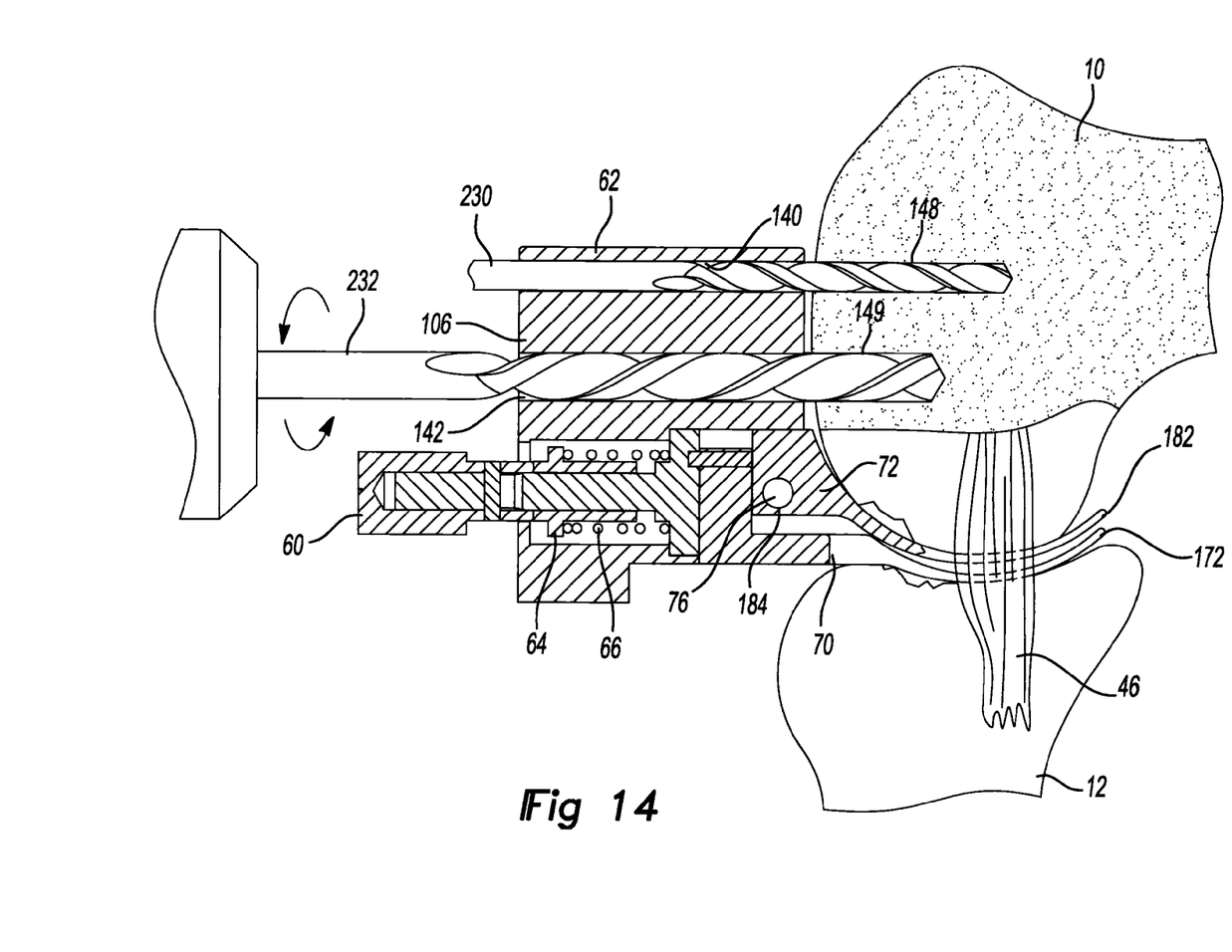
FIG. 14 is a medial view of the knee shown in FIG. 13 and illustrated with a first and second drill bit drilling peg holes into the femur while being guided along respective bores formed through the adjustable femoral drill guide.

Once the surgeon has determined the desired offset between the respective tibial and femoral spoons 70 and 72, the femoral peg holes 148, 149 can be prepared into the femur 10. The lug hole 149 can receive the peg 40. The lug hole 148 can be provided for receiving a peg of other femoral implants that may incorporate two pegs. Additionally, or alternatively, the lug hole 148 can be used with the lug hole 149 to facilitate rotational stability of the femoral drill guide body 62. With reference to FIG. 14, a first drill bit 230 can be guided through the throughbore 140 of the tower 106 on the femoral drill guide body 62 for preparation of the first hole 148. Similarly, a second drill bit 232 can be guided through the second throughbore 142 in the tower 106 of the femoral drill guide body 62 for preparation of the second hole 149 in the femur 10. It will be appreciated that during the drilling of the holes 148 and 149 for the femoral pegs 40 and 42, respectively, the locating peg 214 of the IM rod link assembly 200 can be located into the cannulation 55 of the IM rod 54 while the locating peg 219 can be located into one of the connecting holes 136 of the femoral drill guide body 62. Because the shaft 210 of the first locating portion 202 is rotatably received within the cannulation 217 of the second locating portion 204, the relative position between the first and second locating pegs 214 and 219 is variable to accommodate various femoral and tibial spacing of a range of patients. However, in some instances, the IM rod link assembly 200 may not be used. According to one example, the drill bits 230 and 232 can be retained in the holes 148 and 149 prepared in the femur 10 while the IM rod link 202 and IM rod 54 are removed.

Figure 15:
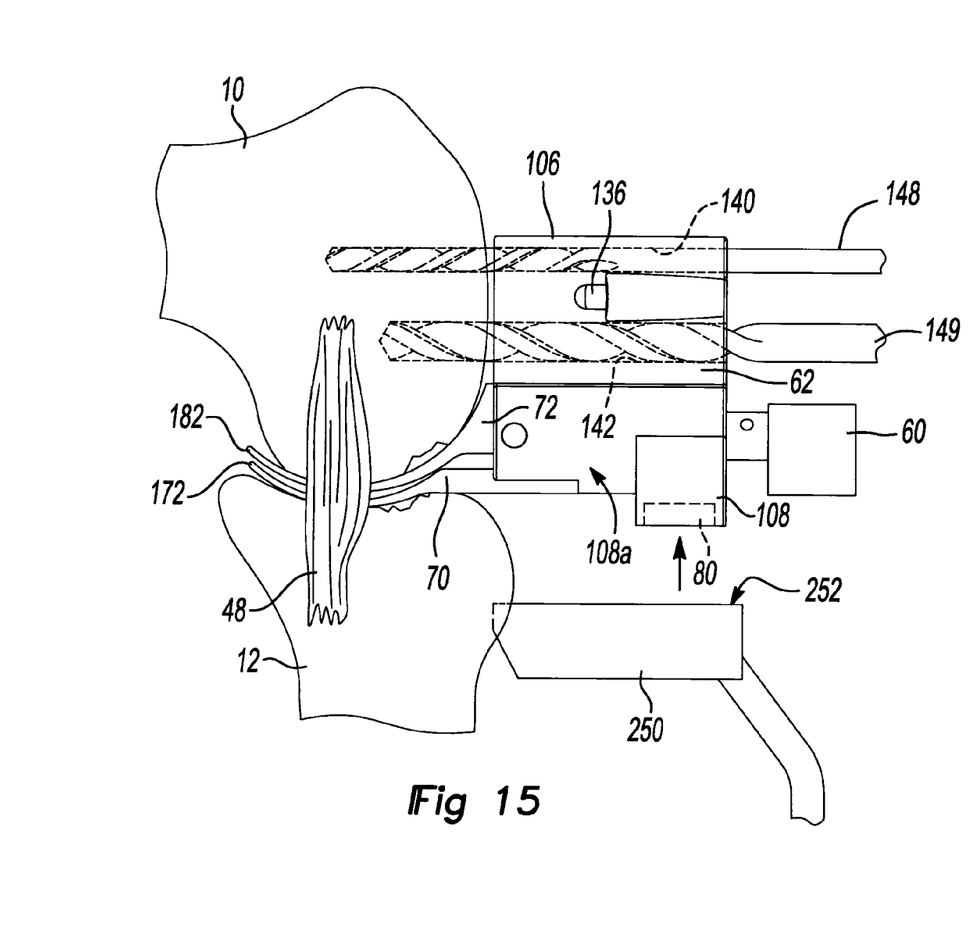
FIG. 15 is a lateral view of the knee shown in FIG. 14 illustrating a tibial cut block being magnetically coupled to the adjustable femoral drill guide.
Figure 16:
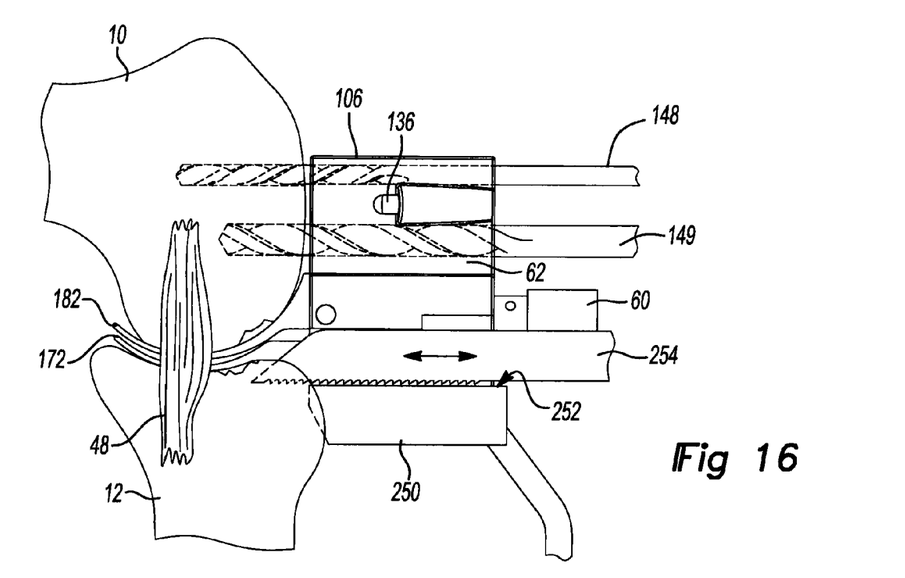
FIG. 16 is a lateral view of the knee joint of FIG. 15 and shown with a saw being guided along a terminal end surface of the femoral drill guide while cutting a superior/inferior cut on the tibial according to one example.
Figure 17:
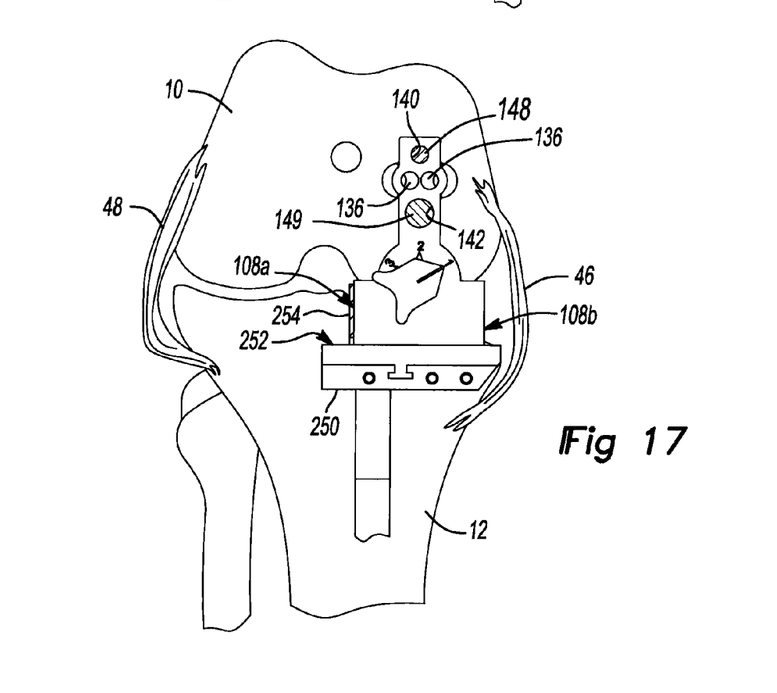
FIG. 17 is an anterior view of the knee joint of FIG. 16 shown with the saw being guided along the terminal end surface of the femoral drill guide.
Figure 18:
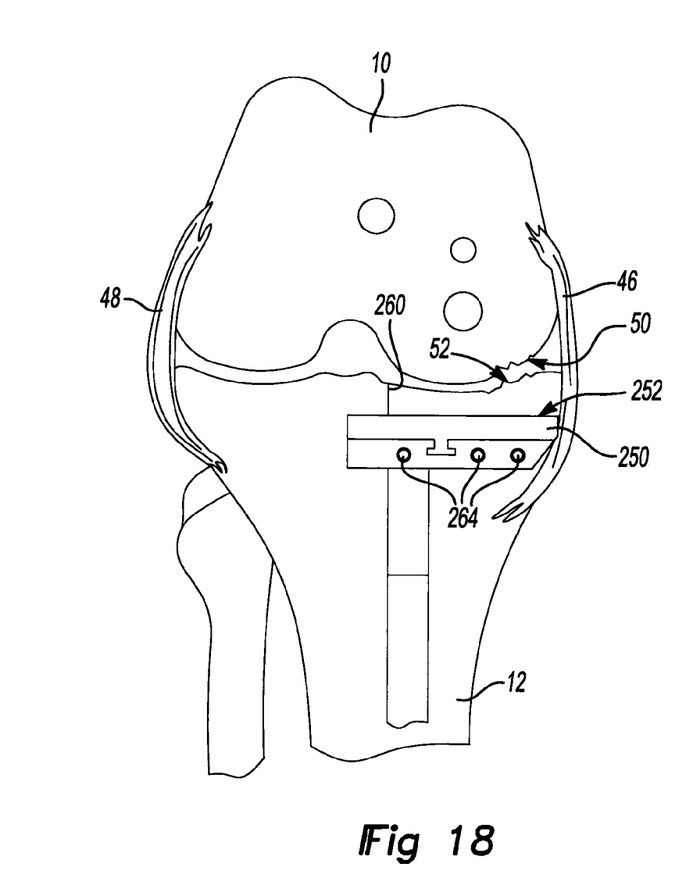
FIG. 18 is an anterior view of the knee of FIG. 16 and shown with the tibial cut block pinned to the tibia and the femoral drill guide removed subsequent to cutting the superior/inferior cut on the tibia.
Figure 20:
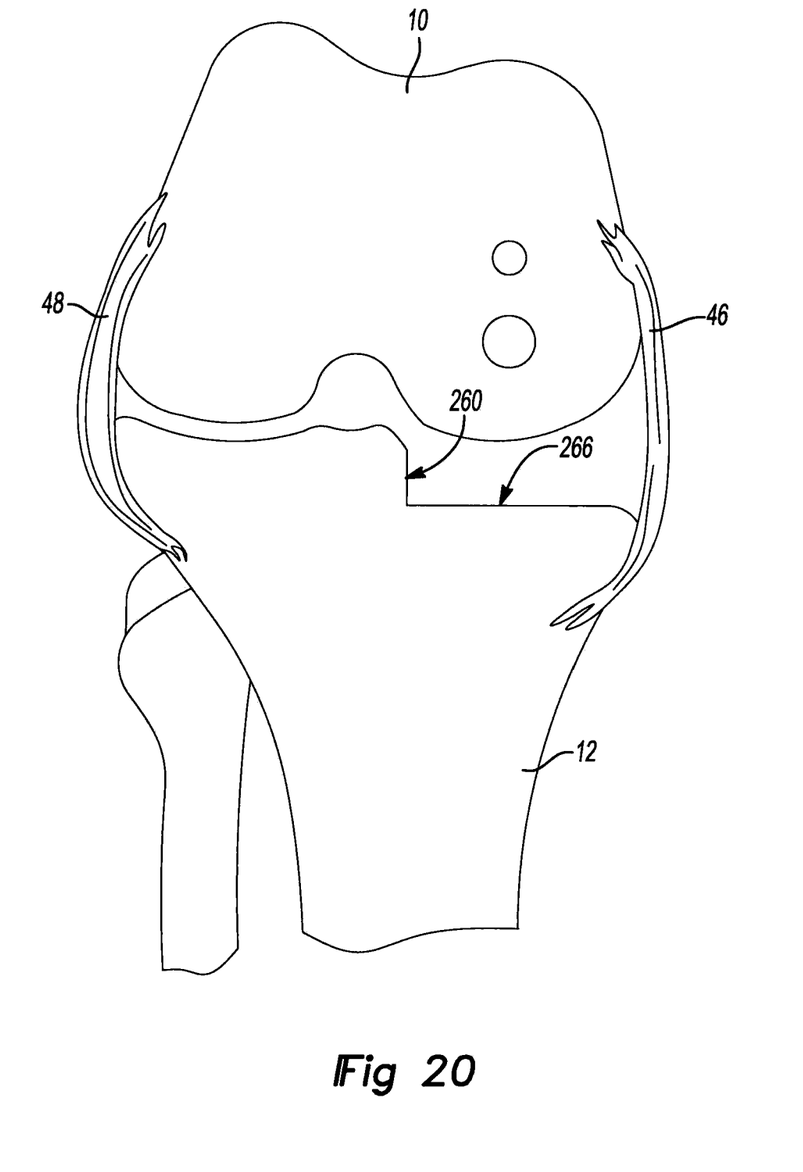
FIG. 20 is an anterior view of the knee shown in FIG. 18 and illustrated subsequent to performing both of the superior/inferior and medial/lateral cuts on the tibia for receipt of the tibial unicondylar prosthesis.

Turning now to FIGS. 15-17, a surgeon can couple a tibial cut guide 250 to the base 107 of the femoral drill guide body 62, while the drill bits 230 and 232 are retained in the bone holes 148 and 149. According to one example, the tibial cut guide 250 can be magnetically coupled to the base 107 using the magnets 80. Specifically, an upper surface 252 can magnetically engage the lower surface 133 of the femoral drill guide body 62. Once the tibial cut guide 250 is coupled to the femoral drill guide body 62, the tibial cut guide 250 can be fixed relative to the tibia 12, such as by way of pins 264. A cutting instrument 254 can then be used to prepare a vertical (i.e., superior/inferior) cut 260 in the tibia 12. The cutting instrument 254 can reference (engage) the terminal medial cutting surface 108a while making the vertical cut 260 (see also FIG. 18). Because the tibial cut guide 250 extends more laterally than the terminal medial cutting surface 108a, the upper surface 252 can act as a stop surface for the vertical cut 260. The upper surface 252 can therefore set a depth of cut for the vertical cut 260. Once the vertical cut 260 has been prepared in the tibia 12, the drills 230 and 232 and the adjustable femoral drill guide body 62 can be removed. (FIG. 18). A cutting instrument 270 can then be used to prepare the horizontal (medial/lateral) cut 266 on the tibia 12 (FIG. 20) while referencing (engaging) the upper surface 252. The tibial cut guide 250 can then be removed and the tibia 12 is ready for receipt of the tibial component 16. The femur 10 can then be cut for receipt of the femoral component 14.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for preparing a femur and a tibia for receipt of a partial knee prosthesis, the method comprising:
   positioning a femoral engagement member of a femoral drill guide proximate to the femur;
   positioning a tibial engagement member of the femoral drill guide proximate to the tibia;
   moving an adjuster associated with the femoral drill guide to translate at least one of the femoral engagement member or the tibial engagement member against the femur or tibia respectively to widen a joint space defined between the femur and the tibia;
   drilling holes in the femur using the femoral drill guide as a reference;
   coupling a tibial cut guide to the femoral drill guide;
   making a first cut in the tibia by referencing the femoral drill guide; and
   making a second cut in the tibia by referencing the tibial cut guide.

2. The method of claim 1, further comprising making the first cut generally perpendicular to the second cut.

3. The method of claim 1, further comprising coupling the tibial cut guide to the femoral drill guide such that a first cutting surface of the femoral drill guide is perpendicular to a second cutting surface of the tibial cut guide.

4. The method of claim 1, wherein moving the adjuster moves a femoral spoon of the femoral engagement member and a tibial spoon of the tibial engagement member.

5. The method of claim 1, wherein drilling holes in the femur using the femoral drill guide includes drilling lug holes in the femur using bores in the femoral drill guide as a reference.

6. The method of claim 1, wherein making a first cut in the tibia by referencing the femoral drill guide includes referencing a terminal cutting surface on the femoral drill guide.

7. The method of claim 1, wherein making the first cut in the tibia includes performing a superior/inferior cut on the tibia using a terminal cutting surface of the femoral drill guide as a reference.

8. The method of claim 7, wherein making the second cut in the tibia includes performing a medial/lateral cut in the tibia using an upper cutting surface of the tibial cut guide as a reference.

9. The method of claim 1, wherein moving the adjuster includes passing a locating finger extending from the adjuster through a first keyway provided on the femoral drill guide, rotating the adjuster around an adjuster axis, and passing the locating finger through a second keyway provided on the femoral drill guide.

10. The method of claim 9, wherein rotating the adjuster around the adjuster axis causes a cam follower fixed to one of the femoral and tibial engagement members to ride along a groove in the cam resulting in one of the femoral or tibial engagement members to move relative to the other.

11. A method for preparing a femur and a tibia for receipt of a partial knee prosthesis, the method comprising:
    coupling a femoral drill guide to an intramedullary rod inserted within the femur;
    positioning a femoral engagement member of a femoral drill guide proximate to the femur;
    positioning a tibial engagement member of the femoral drill guide proximate to the tibia;
    moving at least one of the femoral engagement member or the tibial engagement member against the femur or tibia respectively to widen a joint space defined between the femur and the tibia;
    coupling a tibial cut guide to the femoral drill guide;
    performing a first cut on the tibia while referencing a terminal cutting surface on the femoral drill guide; and
    performing a second cut on the tibia while referencing the tibial cut guide.

12. The method of claim 11, further comprising drilling lug holes in the femur using bores defined by the femoral drill guide as a reference.

13. The method of claim 11, wherein performing the first cut on the tibia includes performing a superior/inferior cut on the tibia using the terminal cutting surface as a first reference; and
    wherein performing the second cut on the tibia includes performing a medial/lateral cut on the tibia using an upper cutting surface of the tibial cut guide as a reference.

14. The method of claim 11, further comprising moving an adjuster disposed on the femoral guide to move at least one of the femoral engagement member or the tibial engagement member.

15. A method for preparing a femur and tibia for receipt of a partial knee prosthesis, the method comprising:
    locating a femoral drill guide adjacent a femur wherein a femoral engagement member associated with the femoral drill guide is positioned proximate the femur and a tibial engagement member associated with the femoral drill guide is positioned proximate the tibia;
    moving an adjuster disposed on the femoral drill guide causing at least one of the femoral and tibial engagement members to translate against the respective femur and tibia causing a joint space between the femur and tibia to widen;
    determining a desired joint space between the femur and tibia based on the translation;
    drilling lug holes in the femur using bores in the femoral drill guide as a reference;
    coupling a tibial cut guide having an upper cutting surface to the femoral drill guide;
    performing at least one cut on the tibia while referencing a terminal cutting surface on the femoral drill guide; and
    performing at least one cut on the tibia while referencing the tibial cut guide.

16. The method of claim 15, wherein performing the cuts on the tibia comprises:
    performing a superior/inferior cut on the tibia using the terminal cutting surface as a reference; and
    performing a medial/lateral cut on the tibia using the upper cutting surface of the tibial cut guide as a reference.

17. The method of claim 15, wherein moving the adjuster comprises passing a locating finger extending from the adjuster through a first keyway provided on the femoral drill guide, rotating the adjuster around an adjuster axis and passing the locating finger through a second keyway provided on the femoral drill guide; and
    wherein rotating the adjuster around the adjuster axis causes a cam follower fixed to one of the femoral and tibial engagement members to ride along a groove in the cam resulting in one of the femoral and tibial engagement members to move relative to the other of the femoral and tibial engagement members.

18. The method of claim 15, further comprising:
    coupling an intramedullary (IM) rod link between the femoral drill guide and an IM rod extending from the femur to align the femoral drill guide relative to the IM rod prior to drilling the lug holes.

19. The method of claim 18, further comprising:
leaving a drill bit in one of the lug holes;
removing the IM rod link; and
subsequently performing the superior/inferior cut on the tibia;
subsequently removing the femoral drill guide; and
subsequently performing the medial/lateral cut on the tibia.

20. The method of claim 15, wherein coupling the tibial cut guide comprises magnetically coupling the tibial cut guide to the femoral drill guide.

* * * * *